United States Patent [19]

Lozier

[11] Patent Number: 4,759,352
[45] Date of Patent: Jul. 26, 1988

[54] INSTRUMENT FOR INSERTING A LOCKING PIN

[75] Inventor: Anthony J. Lozier, Warsaw, Ind.

[73] Assignee: Zimmer, Inc., Warsaw, Ind.

[21] Appl. No.: 928,765

[22] Filed: Nov. 10, 1986

[51] Int. Cl.$^4$ .................................................. A16F 5/04
[52] U.S. Cl. ............................. 128/92 YS; 128/92 YV
[58] Field of Search .......... 128/92 YS, 92 YV, 92 YT

[56] References Cited

U.S. PATENT DOCUMENTS

| | | | |
|---|---|---|---|
| 2,570,465 | 10/1951 | Lundholm | 128/92 YV |
| 3,374,786 | 3/1968 | Callender, Jr. | 128/92 YV |
| 4,095,591 | 6/1978 | Graham, Jr. et al. | 128/92 YV |
| 4,530,355 | 7/1985 | Griggs | 128/92 YS |

FOREIGN PATENT DOCUMENTS 2406068  6/1980  Fed. Rep. of Germany ........ 128/92 YV

OTHER PUBLICATIONS

Compression Hip Screw Systems, 1975.

*Primary Examiner*—C. Fred Rosenbaum
*Assistant Examiner*—Mark F. Colosimo
*Attorney, Agent, or Firm*—Paul David Schoenle

[57] ABSTRACT

An instrument for inserting a locking pin in a hip screw assembly, includes a handle with a cavity and a rod extends outwardly from the cavity to carry the locking pin and provide for alignment during insertion of the locking pin in a barrel of a tube plate. The rod is collapsible within the cavity to provide a compact instrument for easy manipulation by a surgeon.

7 Claims, 2 Drawing Sheets

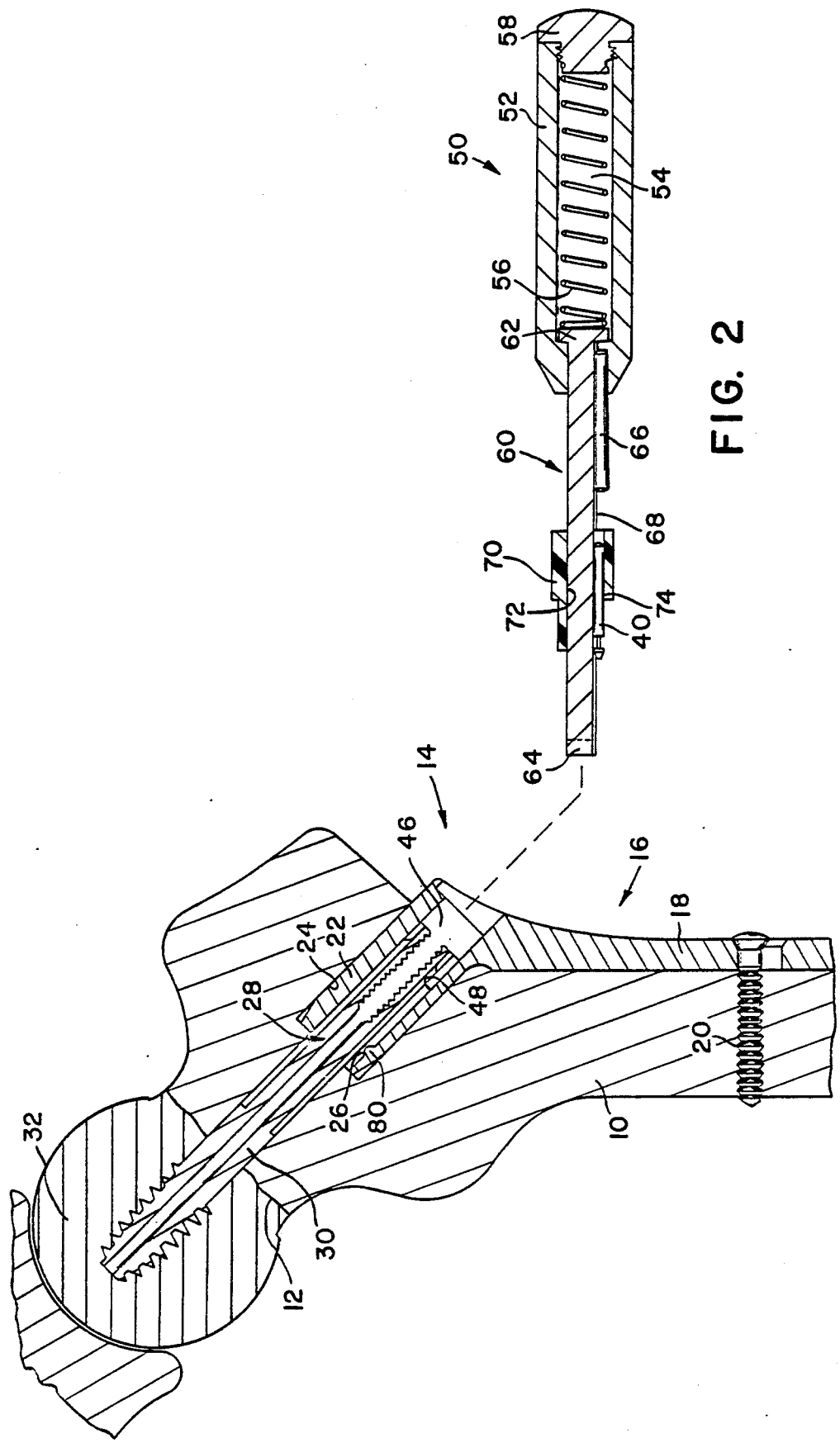

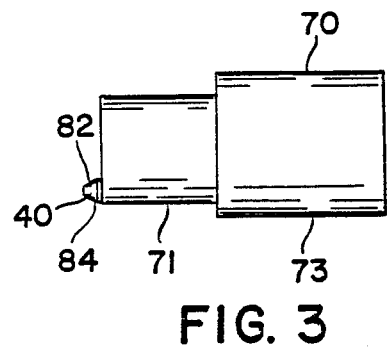
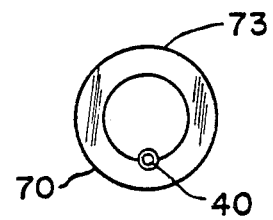
FIG. 3
FIG. 4
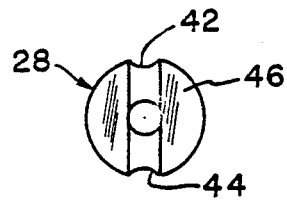
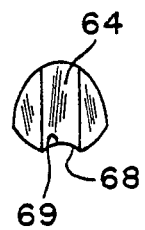
FIG. 5
FIG. 6

INSTRUMENT FOR INSERTING A LOCKING PIN

The present invention relates to an instrument for inserting a locking pin into a hip screw assembly. The locking pin cooperates with a screw and a barrel to oppose rotation therebetween.

In U.S. Pat. No. 4,530,355, a compression hip screw assembly includes a lag screw for insertion into a femoral head and a tube plate for attachment to the femoral stem. The barrel defines a bore for receiving the lag screw and a flexible clip is inserted in the barrel to oppose rotation between the barrel and the lag screw. In order to insert the flexible clip into the barrel, a wrench carries the flexible clip via a holder and a pusher on the wrench is activated to push the flexible clip into the barrel. The pusher slides on the outer surface of the wrench which extends a substantial distance from the lag screw to accommodate the barrel portion of a tube plate. Consequently, a surgeon utilizing this wrench must manually control numerous parts simultaneously while also maintaining the lengthy wrench in alignment with an opening in the femoral head, thereby creating a cumbersome procedure for the surgeon.

The present invention provides a simple instrument to insert a locking pin in a hip screw assembly. The instrument is provided solely for insertion of the locking pin so that the lag screw and tube plate do not complicate the method for utilization of the instrument. Moreover, the instrument is designed to collapse during insertion of the locking pin, thereby resulting in a shorter instrument during insertion for easy manipulation by the surgeon. The instrument includes a handle with a cavity adapted to receive a rod during insertion of the locking pin. A finger extends outwardly from the handle to align the rod with the handle and also to engage the locking pin. When the handle is pushed toward the lag screw, the rod is movable into the cavity and the finger pushes the locking pin relative to the rod to dispose it into a barrel of a tube plate in matching grooves on the barrel and the lag screw.

It is an object of the present invention to provide a simple instrument for insertion of a locking pin which is compact for easy manipulation by a surgeon and which is not dependent upon the disposition of a lag screw and a tube plate at the sight of fracture adjacent a femoral head or neck.

Turning to the drawings,

FIG. 1 is a side view of a hip screw as applied to a femur having a fracture at the neck.

FIG. 2 is a cross-sectional view of the instrument of the present invention.

FIG. 3 is a side view of a sleeve which releasably carries a locking pin.

FIG. 4 is an end view of FIG. 3.

FIG. 5 is an end view of the lag screw, and

FIG. 6 is an end view of a rod comprising a part of the instrument.

When a femur 10 is fractured at the neck as illustrated in FIG. 1 at line 12, it is conventional orthopaedic practice to utilize a hip screw assembly 14 to reduce the fracture and provide stabilization while the fracture mends itself and the bone grows back together. The hip screw assembly 14 includes a tube plate 16 with a plate 18 extending posteriorly along the stem of the femur and secured thereto by bone screws 20, only one of which is illustrated. The plate 18 terminates superiorly in a barrel 22 which fits into a cylindrical opening 24.

The barrel defines a bore 26 to receive a lag screw 28 which extends across the fracture 12 for fixation via threads 30 to the femoral head 32. Such a hip screw is further described in U.S. Pat. No. 4,612,920 issued to Jerry Lower on Sept. 23, 1986.

When the lag screw 28 is secured to the femoral head and the tube plate is secured to the femoral stem, it is sometimes desirable to prevent rotation between the lag screw 28 and barrel 22. Consequently, a locking pin 40 may be inserted between the lag screw 28 and the barrel 22. To accommodate the locking pin 40, the lag screw is provided with slots 42 and 44 extending longitudinally from a slotted end 46 while the barrel 22 is provided with a matching slot 48 on the bottom or posterior side. The locking pin 40 fits into the barrel slot 48 and one of the lag screw slots 42 and 44 to prevent rotation between the lag screw 28 and the barrel 22.

In order to dispose the locking pin 40 between the lag screw 28 and the barrel 22 an instrument 50 is designed to carry the locking pin and align the latter with slot 48 before moving the locking pin into the slot 48. The instrument 50 includes a handle 52 with a cavity 54 receiving a spring 56. A cap 58 closes the cavity at one end and is removable to permit assembly of the spring 56 into the cavity 54. A rod 60 extends outwardly from the handle 52 opposite the cap 58. The rod 60 forms an enlarged end 62 engageable with spring 56 and a tip 64 adapted for attachment to the slotted end 46 of lag screw 28. In addition, the handle 52 fixedly carries a finger 66 extending in the same direction as the rod 60. The rod 60 defines a groove 68 extending to the end of the tip 64 for partially receiving a minor portion of the finger 66. As shown in FIG. 6 the tip is substantially rectangular with the groove formed on a minor side 69 of the rectangle. The finger 66 cooperates with the groove 68 to prevent rotation of the rod 60 relative to the handle. Consequently, the handle and rod can be utilized in a screw driver fashion to rotate the lag screw when the tip is engaged with the slotted end 46. A sleeve 70 defines a bore 72 receiving the rod 60 and a recess 74 extending over the length of the sleeve 70 to partially receive the locking pin 40 prior to insertion into the barrel 22. A substantial portion of the locking pin 40 is disposed in the recess 74 with a minor portion extending into the bore 72. In order to slip the sleeve 70 and locking pin 40 over the rod 60 from the tip 64, the locking pin 40 is first disposed in the recess 74 and then the locking pin is aligned with the groove 68 before the sleeve and locking pin are fitted over the rod for juxtaposition the finger 66.

With the sleeve 70 and locking pin 40 carried by the rod 60, the surgeon grabs the handle 50 to fit tip 64 into the slotted end 46 of lag screw 28. The surgeon next imparts rotation to the lag screw, if necessary, to align either slot 42 or 44 with the slot 48. At that time, the groove 68 is also aligned with either slot 42 or 44 because the groove 68 is centrally disposed on the tip 64 and the lag screw slot 42 and 44 intersect the slotted end 46. The locking pin 40 is disposed in the sleeve to extend slightly outwardly of the sleeve 70 so that it is possible to push the handle and collapse the rod into the cavity to engage the tip of locking ring 40 with the barrel 22. With the locking pin 40 engaging the barrel slight rotation of the handle will also rotate the lag screw until the tip of the locking ring 40 is aligned with the slot 48. Since the locking pin is already in alignment with either slot 42 or 44, the surgeon continues pushing on the handle 50 to further collapse the rod 60 within the cavity 54. The finger 66 abuts the locking pin 40 to move the latter outwardly from the sleeve 70 and into the slot 48 and either slot 42 or 44. The length of the finger extending outwardly of the handle 50 is greater than the length of the sleeve so that the locking pin will be fully removed from the sleeve 70 for disposition in the barrel 22. The slot 48 includes a projection 80 and the forward end of the locking pin 40 is slotted to define flexible tongs 82 and 84 which can pass over the projection 80 during insertion and oppose withdrawal of the locking pin 40 from the slot 48 in a longitudinal direction. With the locking pin disposed in the barrel in engagement with the lag screw, the surgeon merely pulls the handle away from the tube plate leaving the locking pin in its operable position within the barrel. The spring 56 biases the rod to extend outwardly from the handle so that another sleeve and locking pin can be fitted over the rod in preparation for subsequent surgery involving a hip screw assembly.

The sleeve 70 as shown in FIGS. 1, 3 and 4 includes a first diameter 71 and a second diameter 73 larger in dimension than the first diameter. The locking pin 40 is exposed at the first diameter to visually verify its position in the sleeve and the second diameter surrounds the locking pin to retain the latter in the sleeve recess 74.

In view of the foregoing description it is seen that the instrument provides a compact assembly for manipulating the locking pin into its operable position within the barrel.

What is claimed is:

1. An instrument assembly for inserting a locking pin in a hip screw assembly wherein the locking pin cooperates with a screw and a barrel which forms an opening to receive the screw, the instrument assembly including a handle for manual orientation, a rod extending outwardly from the handle and telescopically disposed relative to the handle, the handle defining a cavity receiving resilient means biasing the rod outwardly from the handle, a finger engaging the handle and cooperating with the rod to oppose rotation of the rod relative to the handle, and a sleeve movably carried by the rod and releasably carrying the locking pin, the rod including means cooperating with the screw to align the locking pin relative to the screw and the means further being adapted to rotate the screw relative to the barrel such that movement of the handle relative to the rod engages the finger with the locking pin to insert the latter into the barrel in engagement with the screw and the barrel to oppose rotation therebetween while the rod is collapsed into the cavity to compactly arrange the rod and handle during insertion of the locking pin.

2. The instrument assembly of claim 1 in which the sleeve defines a first diameter smaller in dimension than a second diameter and the locking pin is exposed at the first diameter and covered at the second diameter.

3. The instrument assembly of claim 1 in which the handle defines a recess at one end from which the rod extends and the finger is fixedly disposed within the handle recess.

4. The instrument assembly of claim 1 in which the rod is yieldably biased to a position extending outwardly from the handle.

5. The instrument assembly of claim 1 in which the rod defines a groove extending from an end of the rod to the handle and the finger is partially disposed in the groove.

6. The instrument assembly of claim 5 in which the sleeve carries the locking pin in order to partially dispose the locking pin in the groove, and the locking pin extends outwardly from the sleeve in the direction of the rod cooperating means.

7. The instrument assembly of claim 5 in which the rod terminates in a substantially rectangular tip and the groove intersects only one minor side of the rectangle.

* * * * *

UNITED STATES PATENT AND TRADEMARK OFFICE
Certificate

Patent No. 4,759,352                                          Patented: July 26, 1988

On petition requesting issuance of a certificate for correction of inventorship pursuant to 35 U.S.C. 256, it has been found that the above-identified patent, through error and without any deceptive intent, improperly sets forth the inventorship. Accordingly, it is hereby certified that the correct inventorship of this patent is: Antony J. Lozier.

Signed and Sealed this Eighteenth Day of June, 1991.

FRED ROSENBAUM

*                                                                                       S. P. E.*
*                                                                        Art Unit 336*

UNITED STATES PATENT AND TRADEMARK OFFICE
Certificate

Patent No. 4,759,352                                                                Patented: July 26, 1988

On petition requesting issuance of a certificate for correction of inventorship pursuant to 35 U.S.C. 256, it has been found that the above-identified patent, through error and without any deceptive intent, improperly sets forth the inventorship. Accordingly, it is hereby certified that the correct inventorship of this patent is:
Antony J. Lozier, Warsaw, Ind; Jerry L. Lower, Bourbon, Ind.

Signed and Sealed this Twenty-ninth Day of October, 1991.

C. FRED ROSENBAUM

*Supervisory Patent Examiner*
*Group 330*